United States Patent [19]

Amiel

[11] Patent Number: 5,342,350
[45] Date of Patent: Aug. 30, 1994

[54] METHOD OF ENDOSCOPICALLY TREATING LITHIASES WITH A MULTICHANNEL PROBE SUITABLE FOR DRAINING THE TREATED LITHIASES

[76] Inventor: Jean Amiel, Villa "Christiane"-11, avenue du Cap de Nice, 06300 Nice, France

[21] Appl. No.: 655,601

[22] Filed: Feb. 15, 1991

[30] Foreign Application Priority Data

Feb. 16, 1990 [FR] France ................ 90 02219
Feb. 19, 1990 [FR] France ................ 90 01981

[51] Int. Cl.⁵ ........................................... A61M 5/02
[52] U.S. Cl. ................................ 606/2.5; 606/15; 606/128; 128/898; 604/96; 607/89
[58] Field of Search .......... 128/395, 392, 398, 898; 606/2-7, 10-18, 127, 128, 2.5; 604/96; 607/89

[56] References Cited

U.S. PATENT DOCUMENTS

| | | | |
|---|---|---|---|
| 4,069,823 | 1/1978 | Isakov et al. | 606/11 |
| 4,445,892 | 5/1984 | Hussein et al. | 606/15 |
| 4,583,539 | 4/1986 | Karlin et al. | 606/19 |
| 4,648,892 | 3/1987 | Kittrell et al. | 606/7 |
| 4,721,115 | 1/1988 | Owens | 604/96 |
| 4,744,360 | 5/1988 | Bath | 606/6 |
| 4,800,876 | 1/1989 | Fox et al. | |
| 4,887,600 | 12/1989 | Watson et al. | 606/15 |
| 4,911,711 | 3/1990 | Telfair et al. | 606/5 |

FOREIGN PATENT DOCUMENTS

| | | | |
|---|---|---|---|
| 91334 | 10/1983 | European Pat. Off. | 606/4 |
| 253734 | 1/1988 | European Pat. Off. | 606/10 |
| 0266928 | 5/1988 | European Pat. Off. | |
| 0370115 | 12/1989 | European Pat. Off. | |
| 0350021 | 1/1990 | European Pat. Off. | |
| 2809007 | 9/1974 | Fed. Rep. of Germany | 606/10 |
| 3043533 | 6/1981 | Fed. Rep. of Germany | 606/18 |
| 85209732 | 10/1985 | Fed. Rep. of Germany | |
| 8912479 | 6/1989 | PCT Int'l Appl. | |
| 1073914 | 6/1985 | U.S.S.R. | 606/10 |
| 8702884 | 5/1987 | World Int. Prop. O. | 606/3 |

*Primary Examiner*—David M. Shay
*Attorney, Agent, or Firm*—Stroock & Stroock & Lavan

[57] ABSTRACT

A multichannel probe comprising a hollow tube defining a distal end and a proximal end, the tube being made of a flexible self-supporting material enabling the tube to fold or to be curved, and said hollow tube being subdivided into at least three independent longitudinal channels by at least two internal partitions disposed longitudinally substantially parallel to the axis of symmetry of the tube.

6 Claims, 1 Drawing Sheet

METHOD OF ENDOSCOPICALLY TREATING LITHIASES WITH A MULTICHANNEL PROBE SUITABLE FOR DRAINING THE TREATED LITHIASES

FIELD OF THE INVENTION

The present invention relates essentially to a multichannel probe having at least three independent longitudinal channels and suitable for use in endoscopically destroying lithiases and also for destroying inorganic deposits in ducts.

The multichannel probe may constitute a catheter for performing endoscopic diagnosis and also treatment of stony obstructions (lithiases) in the body, and more particularly the lithiases encountered in urology and gastroenterology.

The multichannel probe may also be used in fields other than medicine, whenever there is a need to destroy inorganic deposits in ducts that are accessible from an end opening only, with the destruction being performed under remote control.

BACKGROUND OF THE INVENTION

Document U.S. Pat. No. 4,800,876 (Fox) discloses a catheter comprising a tube containing optical fibers for laser radiation treatment and optical fibers for observation, which fibers are fixed inside the tube.

Similarly, Document WO-A-89/12479 Optimed describes a catheter for angioplasty containing an optical fiber which is fixed in permanent manner to said catheter which also has a balloon for increasing its outside diameter.

Document EP-A-0 350 021 discloses the destruction of surface contaminants by direct irradiation using a high energy source that may comprise a pulse layer.

The solutions proposed do not give full satisfaction. In particular, in the medical field of destroying lithiases, in particular as encountered in urology and in gastroenterology, presently available endoscopic devices are constituted by a body which is rigid, semi-rigid, or flexible and in which the optical system is incorporated in non-removable manner. The body generally includes an operating channel for conveying the laser fiber and the washing liquid required for proper operation of the apparatus.

After destroying lithiases, the endoscopic treatment probe is withdrawn and it is then necessary to place a ureteral drainage probe on a temporary basis in the urine excretion path. This complicates the procedure, considerably increasing the total time required for the operation, thus making it unsuitable for proceeding without a general anesthetic and consequently requiring hospitalization.

In addition, present endoscopic devices are very expensive and therefore cannot be discarded after one use only, which means they suffer sterilization problems, in particular problems of sterilizing the operating channel.

In addition, because of the fineness required for these endoscopic devices, they are very fragile which means that their lifetime is relatively short and that they are expensive to maintain.

SUMMARY OF THE INVENTION

An object of the present invention is thus to solve the novel technical problem consisting in providing a solution enabling lithiases to be destroyed while shortening the time required for the entire operation and consequently avoiding the need for a general anesthetic.

Another object of the invention is to solve the novel technical problem consisting in providing a solution ! enabling lithiases to be destroyed by means of a device which is cheaper and less fragile, and which is easy to sterilize or Is suitable for discarding after one use only.

Another object of the present invention is to solve the novel technical problem consisting in providing a solution enabling lithiases to be destroyed by means of an endoscopic device which is also suitable for use on a temporary basis to provide drainage after destroying said lithiases.

Another object of the present invention is to solve the novel technical problem consisting in providing a solution that also makes it possible to destroy inorganic deposits in ducts that can be accessed only from the end, with the destruction treatment being performed under remote control because of the inaccessibility of the deposit.

All of these problems are solved by the present invention in a manner which is simple, cheap, reliable, and of industrial application.

To this end, in a first aspect, the present invention provides a multichannel probe comprising a hollow tube defining a distal end and a proximal end, the tube being made of a flexible self-supporting material enabling the tube to fold or to be curved, and said hollow tube being subdivided into at least three independent longitudinal channels by at least two internal partitions disposed longitudinally substantially parallel to the axis of symmetry of the tube.

In a presently-preferred, advantageous variant, the above-specified multichannel probe is subdivided into four independent channels by at least three internal partitions disposed longitudinally and substantially parallel to the axis of symmetry of the tube.

In another advantageous embodiment of the invention, two of said channels are "small" channels having a smaller diameter than the remaining channel(s) which is/are "large" channel(s).

In another advantageous embodiment, two of said channels are "small" channels and are of smaller diameter than the two remaining channels which are "large" channels, the disposition of the internal partitions preferably constituting a probe structure which is symmetrical about at least one plane of symmetry.

In a particular variant, an internal partition is disposed along a diameter and extends all the way across the tube, and two internal partitions extend from said diametral internal partition to define the two above-specified small channels.

In a particular variant, two small channels have a diameter which is equal to about one half the diameter of the large channel(s).

In a particular variant, one of the channels, in particular a "small" channel, is a "treatment" channel and is intended to receive temporarily an optical fiber adapted to receive laser radiation, and in particular radiation from a pulse laser.

In another particular variant, a "large" one of the channels is an "observation" channel, and is intended to receive temporarily an optical fiber for receiving light radiation for observing and illuminating the zone outside the tube and in the vicinity of its distal end, in particular to form a video image.

In yet another particular variant, one of the channels, in particular a "small" channel, is an "irrigation" channel for receiving an irrigation liquid medium or an anesthetic (such as Xylocaine) for the zone outside the tube in the vicinity of its distal end.

In a particularly advantageous embodiment, the probe constitutes a multichannel endocavity catheter for endoscopic diagnosis and/or treatment of lithiases such as those encountered in urology and gastroenterology, said multichannel catheter including four independent channels by virtue of three internal partitions disposed longitudinally and substantially parallel to the axis of symmetry of said catheter, said channels comprising: a "treatment" first channel for temporarily receiving an optical fiber adapted to receive laser radiation, in particular radiation from a pulse laser; an "observation" second channel for receiving an optical fiber adapted to enable the zone outside the catheter in the vicinity of the distal end to be observed, at least; an "irrigation" third channel for receiving an irrigation liquid medium for irrigating the zone outside the distal end; and an "insertion" fourth channel for receiving a guide wire or "leader" for facilitating insertion of the multichannel catheter into a lumen of the body by guiding the catheter.

In another particular variant, the outside surface of the tube is cylindrical and smooth over substantially all of its length, and its distal end tapers.

In yet another particular variant, the above-mentioned proximal end thereof is provided with a liquid-tight coupling for the independent channels, the coupling including supply or insertion ducts that are optionally removable or detachable and that enable devices for insertion into the respective channels to be applied thereto and that also enable an irrigation liquid medium to be injected therein.

In another particular variant, the tube is made, at least in part, of a radio-opaque material.

In a second aspect, the present invention also covers the use of the above-specified multichannel probe in the manufacture of apparatus for destroying lithiases by shock waves, in particular by means of a pulse laser, and in particular a dye laser.

In a third aspect, the present invention also covers the use of the above-specified multichannel probe in the manufacture of apparatus for treating inorganic deposits in ducts, e.g. under hostile conditions such as within irradiated structures, for treating sludges inside mechanical units, and for treating inorganic deposits (furring) in steam generator tubes of power stations, but without being limited to those specific applications.

In a fourth aspect, the probe may also be used for performing percutaneous surgery, in particular of the kidney.

In a fifth aspect, the present invention provides a method of endoscopically treating lithiases, the method comprising using an endoscopic probe comprising a hollow tube having a proximal end and a treatment distal end, wherein a hollow tube is provided which is subdivided into at least three independent channels by at least two internal partitions disposed longitudinally and substantially parallel to the axis of symmetry of the tube and extending from its proximal end to its distal end;

at least one "treatment" Optical fiber of a size adapted to be inserted into at least one of said channels and capable of receiving a beam of laser radiation, in particular radiation from a pulse laser;

at least one "observation" optical fiber of a size adapted to be inserted in at least one other channel and suitable for receiving light radiation enabling a zone outside to the tube and in the vicinity of the distal end thereof to be observed;

means for injecting at least one irrigation liquid medium into at least one remaining channel;

said multichannel probe is inserted into a lumen of the body in which a lithiasis is assumed to exist until said distal end comes into contact with said lithiasis;

the optical fiber for receiving laser radiation is inserted into the associated channel;

the optical fiber for transmitting observation light radiation is inserted into its associated channel;

when so desired, an irrigation liquid medium is injected into the irrigation channel by said means for injecting at least one irrigation liquid medium;

the lithiasis is destroyed by using laser radiation transmitted by the optical fiber for receiving the laser radiation while visually monitoring the treatment zone outside the vicinity of the distal end by means of light radiation transmitted by the observation optical fiber; and at the end of lithiasis destruction treatment, the treatment optical fiber receiving the laser radiation and the observation optical fiber are withdrawn, and injection of the irrigation liquid medium is stopped.

In a preferred implementation of the method, the multichannel probe is left in position in said lumen of the body for a predetermined period of time to drain the lumen of the body, possibly after dismantling or detaching a liquid-tight coupling used during the treatment.

In an advantageous implementation of the method, a multichannel probe is provided comprising four independent channels defined by at least three internal partitions disposed longitudinally and parallel to the axis of symmetry of the tube, namely: a "treatment" first channel for receiving a treatment optical fiber adapted to receive laser radiation, in particular radiation from a pulse laser; an "observation" second channel for receiving an observation optical fiber adapted to transmit observation light radiation; an "irrigation" third channel for receiving an irrigation liquid medium; and a "guide" fourth channel for receiving a flexible guide wire or "leader";

the above-mentioned guide wire is inserted, in particular by means of a cytoscope, into the lumen of the body assumed to contain a lithiasis;

the multichannel probe is then inserted into the lumen of the body by inserting the visible free end of the guide wire into the guide fourth channel for receiving the guide wire and by sliding the multichannel probe along the guide wire until the distal end of the multichannel probe makes contact with the lithiasis;

the treatment optical fiber is inserted in the treatment first channel by sliding it along said treatment first channel until it comes into contact with the lithiasis;

the observation optical fiber is inserted into the observation second channel and is caused to slide until said observation optical fiber comes into the proximity of the distal end of said multichannel probe;

the lithiasis is destroyed by laser radiation, in particular radiation from a pulse laser while performing visual monitoring by means of the observation optical fiber transmitting light radiation; and at the end of lithiasis destruction treatment, the guide wire is withdrawn.

In an advantageous variant implementation of the method, the lumen of the body is anesthesized locally by injecting an anesthetic into the irrigation channel while the multichannel probe is being slid along the guide wire inside the lumen of the body.

Also, in yet another advantageous variant of the method of the invention, at the end of treatment, after the treatment and observation fibers have been withdrawn, a contrast substance is injected into the irrigation channel to verify that the multichannel probe is properly positioned for the purpose of performing drainage after treatment of the lithiasis, with the multichannel probe being repositioned, if necessary, by sliding along the guide wire, and finally the guide wire is withdrawn when the multichannel probe is deemed to be correctly positioned in the lumen of the body.

When the invention is applied to destroying inorganic deposits, it is performed as specified above in the context of treating lithiases, except insofar as the lumen in the body is replaced by the lumen of a duct containing said inorganic deposits. The inorganic deposits may be present under hostile conditions such as in an irradiated structure, and the method may also be applied to sludges inside mechanical units, and to inorganic deposits (furring) in steam generator tubes in a power station, but without the method being limited to the applications mentioned.

BRIEF DESCRIPTION OF THE DRAWING

An embodiment of the invention is described by way of example with reference to the accompanying drawing, in which.

DETAILED DESCRIPTION

Figure 1:
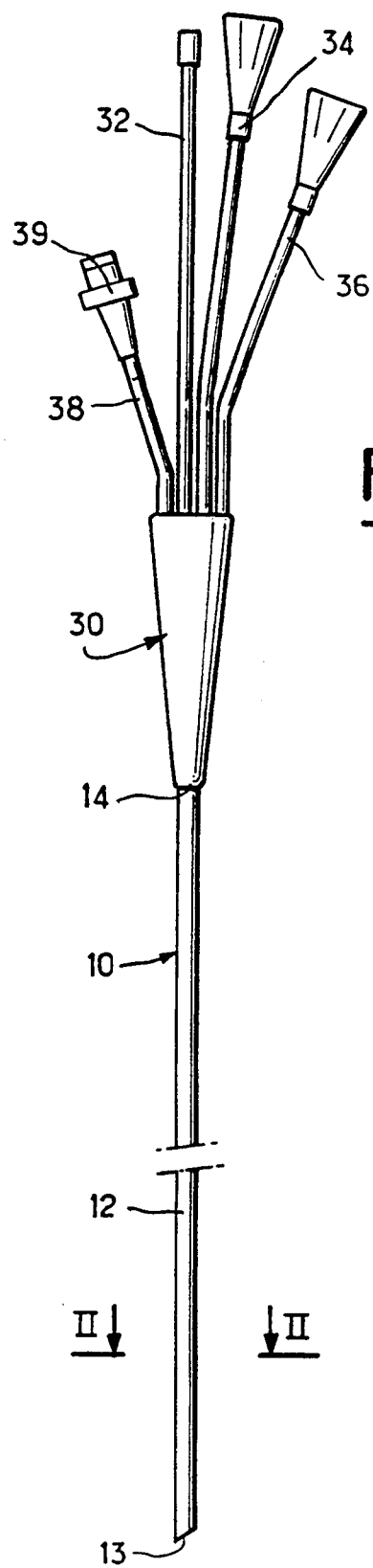
FIG. 1 is a diagrammatic view of the presently-preferred embodiment of a multichannel probe of the present invention and provided with a liquid-tight coupling (optionally removable or detachable) for use in inserting devices into respective ones of the channels and also for use in injecting a liquid irrigation medium.
Figure 2:
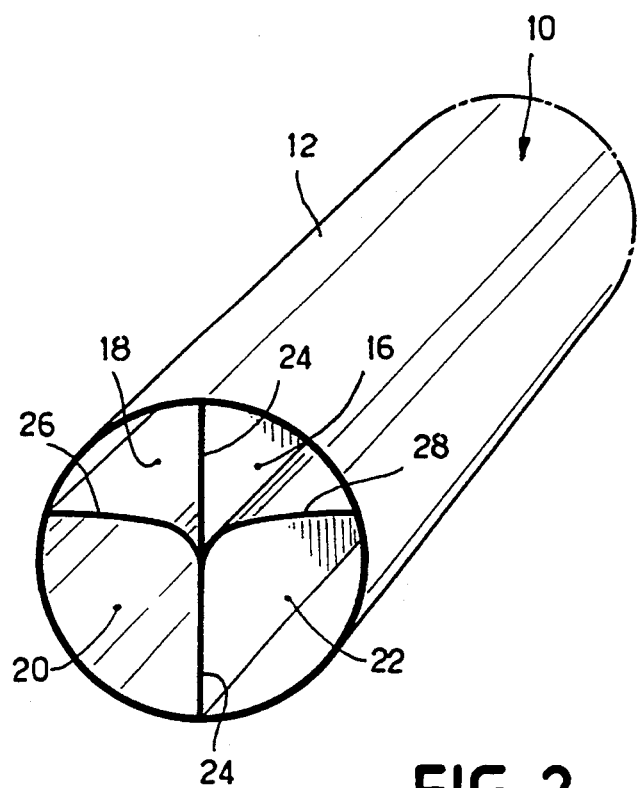
FIG. 2 is a section view on line II—II of FIG. 1.

With reference to FIGS. 1 and 2, a multichannel probe of the present invention is given overall reference numeral 10. This multichannel probe 10 comprises a hollow tube 12 defining a distal end 13 and a proximal end 14.

The multichannel probe is made of a flexible self-supporting material enabling the probe to be folded or curved. Such flexible self-supporting materials are also advantageously biocompatible. Examples include PVC and silicone. The probe may be made radio-opaque by incorporating a radio-opaque filler in said material. Radio-opaque fillers are well known to the person skilled in the art.

In accordance with the invention, the hollow tube 12 is subdivided into at least three longitudinal channels which are independent, i.e. which do not communicate with one another, e.g. channels 16, 18, 20, and 22 which are separated by at least two internal partitions such as 24, 26, and 28 disposed longitudinally substantially parallel to the axis of symmetry of the tube 12.

In a preferred embodiment, as shown in FIG. 2, the multichannel probe 10 has its tube 12 subdivided into four independent channels referenced 16, 18, 20, and 22 respectively, by means of at least three internal partitions respectively referenced 24, 26, and 28 disposed longitudinally and substantially parallel to the axis of symmetry of the tube 12.

In an advantageous variant, two so-called "small" channels (referenced 16 and 18 in this case) are smaller in diameter than the remaining channel or channels which are referred herein as "large" channel(s) referenced 20 and 22 respectively. The disposition of the internal partitions 24, 26, 28 preferably gives the multichannel probe 10 a structure which is symmetrical in at least one plane of symmetry, as shown clearly in FIG. 2, with the plane of symmetry being the plane of the internal partition 24.

In a particular variant, one of the internal partitions, in this case partition 24, lies on a diameter and runs completely across the tube 12, while two other internal partitions, in this case partitions 26 and 28 extend from said diametral partition 24 to define the two above-mentioned small channels 16 and 18.

In a particular advantageous variant, the diameters of the two small channels 16 and 18 are about one-half the diameter of the large channel, or of both large channels referenced 20 and 22.

One of the channels, in particular one of the small channels and in this case channel 16, constitutes a "treatment" channel and is intended to receive temporarily an optical fiber (not shown) suitable for receiving laser radiation and in particular radiation from a pulse laser. Such optical fibers are well known to the person skilled in the art.

Another channel, in particular one of the large channels such as channel 22, constitutes an "observation" channel and may advantageously be intended to receive temporarily an optical fiber or a bundle of optical fibers suitable for forming a video image, as is well known to the person skilled in the art.

In another particular variant, one of the channels, in particular a small channel such as channel 18, is adapted to receive a liquid medium for irrigating the zone outside the tube in the vicinity of its distal end.

One of the channels, in particular a large channel such as the channel 22, is preferably also provided to receive a guide wire or "leader" for facilitating insertion of the multichannel probe 10 into a lumen of the body by guiding the probe.

In yet another particularly advantageous variant, the outside surface of the tube 12 is cylindrical and smooth over substantially all of its length, and its distal end 13 tapers or is fully formed in order to facilitate insertion into a lumen, as can be seen in FIG. 1.

In another particular variant, the proximal end 14 is adapted to receive a liquid-tight coupling given a general reference number 30 enabling the independent channels 16, 18, 20, and 22 to be coupled in leakproof manner to feed or insertion ducts given respective references 32, 34, 36, and 38. Duct 32 serves to guide the optical fiber suitable for receiving laser radiation and consequently it terminates in small channel 16; duct 34 is adapted to receive the observation fiber or the group of optical fibers for reconstituting a video image and consequently it communicates with the corresponding channel, i.e. large channel 22; duct 36 is adapted to receive the guide wire and therefore corresponds with the corresponding channel, in this case large channel 20; and finally duct 38 is adapted to receive the irrigation liquid and thus communicates with small irrigation channel 18.

This multichannel probe and its coupling 30 is suitable for use with any type of laser capable of performing the intended treatment.

Preferred lasers are pulse lasers enabling lithiases or inorganic deposits to be destroyed by shock waves as is now well known to the person skilled in the art. The preferred pulse lasers are dye pulse lasers.

The method of treatment is performed in accordance with the method described above.

In addition, a prototype has been made in which the optical fiber receiving the laser radiation has a diameter of about 300 microns and is easily inserted in small channel 16, while the optical fiber for transmitting light radiation to observe the treatment zone (or the corresponding bundle of optical fibers as is now commercially available) having a diameter of about 500 microns. This optical fiber or bundle of optical fibers maybe fitted outside the coupling 30 with a lens for displaying the lumen. The guide or leader has a diameter of abut 500 microns.

In this way, the outside diameter of the multichannel probe is not more than 7 French Charriere and is suitable for insertion in the urethra without general anesthetic.

Numerous variant embodiments are possible. In particular, the duct 38 for receiving the irrigation liquid medium may include a stop valve 39. The liquid medium injected into the duct 38 and the channel 18 may vary in composition, such that at the beginning of treatment it comprises or includes an anesthetic. The optical fiber for receiving the laser may be replaced by any other device suitable for achieving coagulation or resection providing its outside diameter is compatible with the inside diameter of at least one of the channels 16, 18, 20, and 22. It will also be understood that the channels are to some extent interchangeable with respect to which ones of the above-mentioned functional items they receive.

The multichannel probe of the invention is manufactured very easily.

For example, the extrusion manufacturing technique may be used. Other techniques are well known to the person skilled in the art.

The embodiment shown in FIGS. 1 and 2 constitutes an integral portion of the invention and of the description.

I claim:

1. A method of endoscopically treating inorganic deposits in ducts utilizing a self-supporting elongated hollow flexible tube having a proximal end and a distal end and a longitudinal axis, the tube divided into at least three channels extending along the longitudinal axis of the tube, comprising;
   inserting the distal end of the tube into a lumen of the duct and advancing the tube to the inorganic deposit;
   inserting a laser optical fiber for transmitting laser radiation into one of the channels of the tube and advancing the laser optical fiber to the inorganic deposit;
   inserting an observation optical fiber for transmitting light radiation into one of the channels of the tube and advancing the observation optical fiber to the region of the distal end of the tube;
   selectively injecting an irrigation medium into one of the channels of the tube;
   destroying the inorganic deposit by applying laser radiation to the laser optical fiber while visually monitoring the treatment through the observation optical fiber;
   withdrawing the laser optical fiber and the observation optical fiber at the conclusion of treatment;
   stopping injection of the irrigation medium;
   maintaining the tube in the body lumen of the duct for draining the treated lithiases prior to withdrawing the tube; and
   withdrawing the tube.

2. A method of endoscopically treating lithiases utilizing a multichannel probe of a self-supporting elongated hollow flexible tube having a proximal end and a distal end and a longitudinal axis, the tube divided into at least three channels extending along the longitudinal axis of the tube, comprising:
   inserting the distal end of the tube into a lumen of the body to the lithiases;
   inserting a laser optical fiber for transmitting laser radiation into one of the channels of the tube and advancing the laser optical fiber to the lithiases;
   inserting an observation optical fiber for transmitting light radiation into one of the channels of the tube and advancing the observation optical fiber to the region of the distal end of the tube;
   selectively injecting an irrigation medium into one of the channels of the tube;
   destroying the lithiases by applying laser radiation to the laser optical fiber while visually monitoring the treatment through the observation optical fiber;
   withdrawing the laser optical fiber and the observation optical fiber at the conclusion of treatment;
   stopping injection of the irrigation medium;
   maintaining the tube in the body lumen for draining the treated lithiases prior to withdrawing the tube; and
   withdrawing the tube.

3. The method of claim 2, wherein the tube includes four channels and the method includes first inserting a guide wire into the lumen; inserting the tube onto the guide wire for advancing the tube along the guide wire to the region of the lithiases; and withdrawing the guide wire at the end of the treatment.

4. The method of claim 2, including the step of anesthetizing the lumen by injecting an anesthetic into one channel of the tube as the tube is being introduced and advanced along the lumen.

5. The method of claim 2, including injecting a contrast substance into the tube to verify the position for drainage after treatment of the lithiases.

6. A method of endoscopically and percutaneously treating lithiases utilizing a self-supporting elongated hollow flexible tube having a proximal end and a distal end and a longitudinal axis, the tube divided into at least three channels extending along the longitudinal axis of the tube, comprising:
   inserting the distal end of the tube percutaneously into the body and advancing the tube to the lithiases;
   inserting a laser optical fiber for transmitting laser radiation into one of the channels of the tube and advancing the laser optical fiber to the lithiases;
   inserting an observation optical fiber for transmitting light radiation into one of the channels of the tube and advancing the observation optical fiber to the region of the distal end of the tube;
   selectively injecting an irrigation medium into one of the channels of the tube;
   destroying the lithiases by applying laser radiation to the laser optical fiber while visually monitoring the treatment through the observation optical fiber;
   withdrawing the laser optical fiber and the observation optical fiber at the conclusion of treatment;
   stopping injection of the irrigation medium;
   maintaining the tube in the body lumen for draining the treated lithiases prior to withdrawing the tube; and
   withdrawing the tube.

* * * * *